United States Patent [19]

Kulick

[11] Patent Number: 5,041,077

[45] Date of Patent: Aug. 20, 1991

[54] INTRAVAGINAL INCONTINENCE PROSTHESIS

[76] Inventor: George Kulick, 654 Vine St., Freeland, Pa. 18224

[21] Appl. No.: 603,517

[22] Filed: Oct. 26, 1990

[51] Int. Cl.$^5$ ............................ A61F 2/00; A61F 2/08
[52] U.S. Cl. ...................................... 600/29; 600/31; 623/14; 128/DIG. 25
[58] Field of Search .................................. 600/29–31; 128/DIG. 25, 884, 885; 623/11, 12, 14

[56] References Cited

U.S. PATENT DOCUMENTS

| | | | |
|---|---|---|---|
| 2,638,093 | 5/1953 | Kulick | 128/DIG. 25 |
| 3,554,184 | 1/1971 | Habib | 600/29 |
| 3,646,929 | 3/1972 | Bonnar | 600/29 |
| 3,705,575 | 12/1972 | Edwards | 600/29 |
| 3,709,215 | 1/1973 | Richmond | 606/205 X |
| 4,428,365 | 1/1984 | Hakky | 600/31 |

Primary Examiner—Ronald Frinks
Attorney, Agent, or Firm—H. Jay Spiegel

[57] ABSTRACT

Embodiments of a prosthesis designed to be used to treat female incontinence are disclosed. In each of the embodiments, the prosthesis is of generally U-shaped cross-section, including one leg of the "U" inserted within the vagina and another leg of the "U" engaging against the mons pubis area. The leg which is inserted within the vagina has attached thereto an inflatable balloon designed to be inflated to press against the urethra to compress the urethra against tissue in the rear portion of the symphysis pubis of control urinary incontinence. In one embodiment of the present invention, the entirety of the device is of unitary construction. In a second embodiment, the legs of the "U" are pivotably interconnected to allow adjustment of the relative orientation thereof.

7 Claims, 2 Drawing Sheets

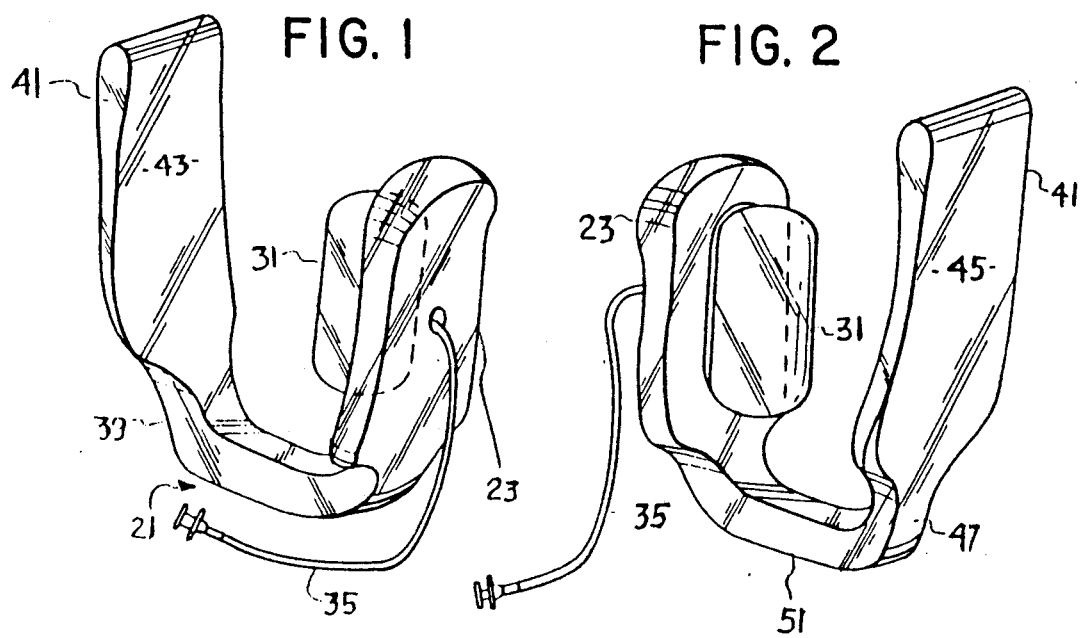
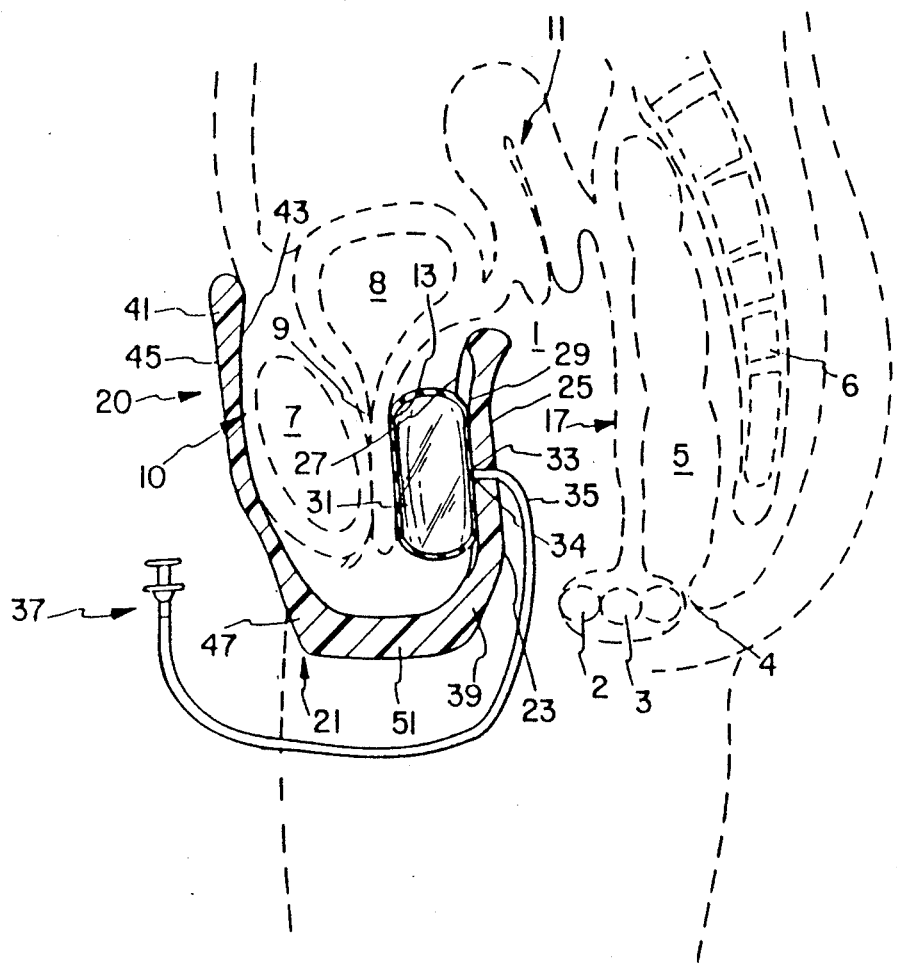

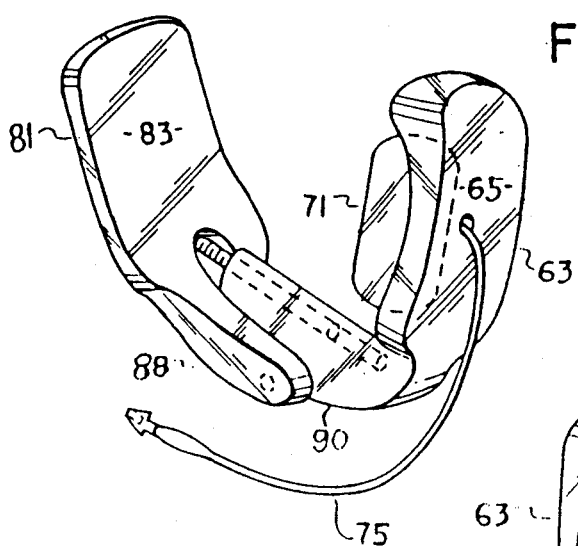
FIG. 4
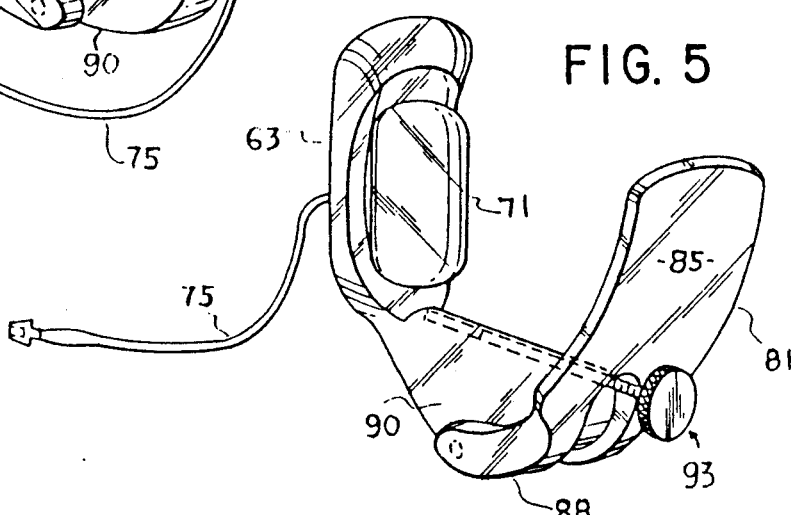
FIG. 5
FIG. 6
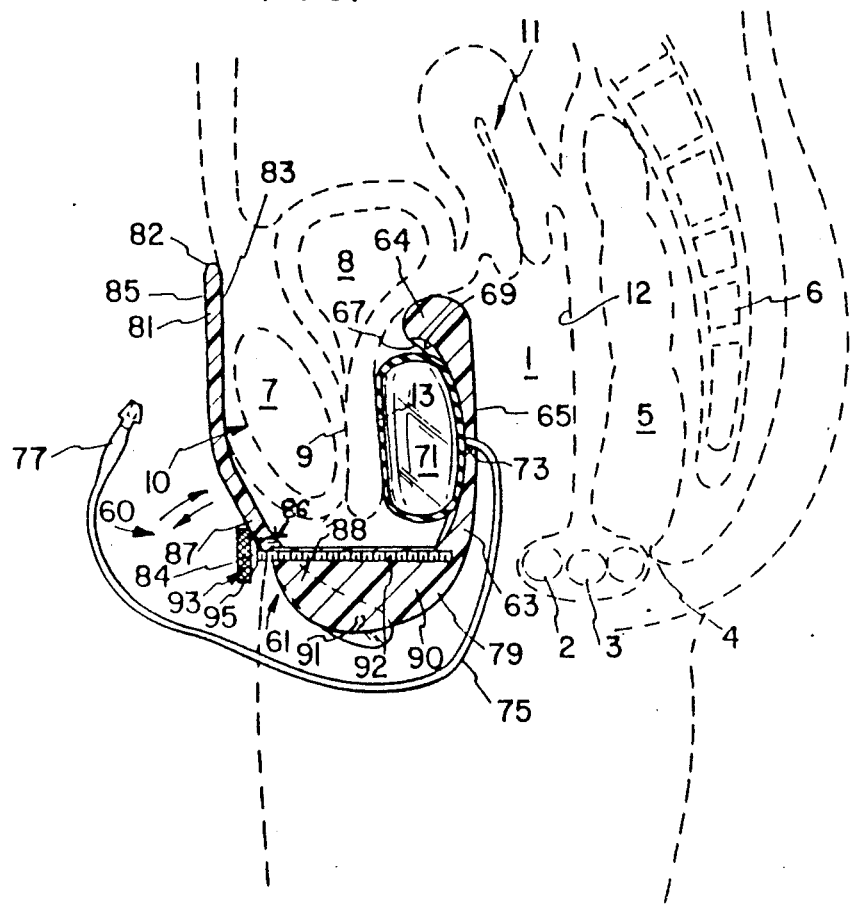

INTRAVAGINAL INCONTINENCE PROSTHESIS

BACKGROUND OF THE INVENTION

According to statistics published by the National Institutes of Health, over ten million Americans ha any one of several types of urinary incontinence. More fifty-percent are women and all age groups are affected.

The complete urinary incontinence of the neurogenic bladder is the worse type for there is no satisfactory surgical procedure to control the urine leakage. An implantable mechanical sphincter-like mechanism with hydraulic control has been developed in recent years. These operations long and difficult and complications sometimes do occur. The whole procedure is very expensive and can be done by a select few urologic surgeons. None of the urinary diversion operations are satisfactory. There are over fifteen the cause of the neurogenic bladder; e.g., spina bifida, mechanical trauma to the spinal cord, viral and bacterial disease of cord, Diabetic neuropathy, tumors, Multiple Sclerosis, Parkinsons Disease, pelvic tumors after resection or radiation general deterioration with advancing age.

The most common type of female incontinence called "Stress Incontinence". Three-fourths of all female patients have this type of incontinence. The main cause is of weakness of stretched or sagging structural tissue in the the pelvis, the bladder, vagina, and/or muscles of the pelvic floor. The angle at the bladder-uretheral junction should be 90°. In prolapsed bladder this angle is lost, then the bladder urinary control mechanism functions poorly. The bladder is capable of holding the urine in if no stress is applied intra-abdominally. Coughing, sneezing, carrying a heavy object will increase the intra-abdominal pressure which in turn transmits the pressure to the urinary bladder. The sphincters cannot hold this extra pressure and some urine is lost. Operations that correct the anatomical defects are generally successful. Recurrence is a problem after a few years and repeat procedures are done. The problems in the female are complex. In the male patients, external catheter mechanisms are an effective means of urinary collection, in the female, no feasible collection receptacle has been devised.

The following prior art is known to Applicant:

The following patents disclose various catamenial devices and are believed to be of only general interest concerning the teachings of the present invention:

U.S. Pat. Nos. 679,478 to Lang, 1,241,652 to Norquist, 1,996,242 to Hagedorn, 3,157,180 to Bakunin, 3,298,369 to Pirie.

U.S. Pat. No. 2,649,086 to Sluijter discloses a ring-like apparatus designed to be inserted within the vagina and including a thickened portion intended to be pressed against the urethra. The present invention differs from the teachings of Sluijter as including a U-shaped appliance having an inflatable bulb associated therewith.

U.S. Pat. No. 2,638,093 to Kulick, Applicant herein, discloses a device designed to be inserted into the vagina and including an inflatable bulb designed to project, when inflated, through an opening therein and to press against the urethra. While this invention has been effective in curing urinary incontinence, the one slight drawback of this invention rests in the ability of the device to be moved away from the front of the vagina adjacent the urethra as the balloon 25 thereof is inflated, due to the ability of the vagina to stretch, thus reducing the pressure which may be exerted against the urethra. The present invention eliminates this problem by providing a U-shaped prosthesis having one leg of the "U" inserted within the vagina and having an inflatable balloon attached thereto, and with the other leg of the "U" resting against the mons pubis to prevent movements of the first-mentioned leg away from adjacency to the urethra during inflation of the balloon. Thus, a measured amount of air injected into the balloon will exert a rather constant pressure.

U.S. Pat. No. 3,419,008 to Plishner is cited as an example of a surgically implanted valve clamp designed to be mounted in surrounding relation to the urethra and to be controlled by external control. Since the present invention does not require surgical intervention and includes many features nowhere taught or suggested by Plishner, Plishner is believed to be of only general background interest.

U.S. Pat. No. 3,334,184 to Habib discloses a pubovaginal incontinence device including two legs, with one leg adapted to be inserted within the vagina and including a curved portion designed to press against the urethra. The other leg is designed to engage the area of the symphysis pubis. The present invention differs from the teachings of Habib as including a U-shaped prosthesis wherein the leg which is inserted within the vagina is specifically sized and configured to snugly fit therein and includes the further provision of an inflatable balloon. Such structure is nowhere taught or suggested by Habib.

U.S. Pat. No. 3,705,575 to Edwards discloses an incontinence device for female use including one leg designed to be inserted within the vagina to exert pressure against the urethra and another leg designed to engage the mons pubis. Edwards further contemplates the application of intermittent electrical current impulses via the device. Again, the present invention differs from the teachings of Edwards as including one leg specifically sized and configured to snugly fit within the vagina and having an inflatable balloon incorporated therewith. These aspects are nowhere taught or suggested by Edwards.

U.S. Pat. No. 3,709,215 to Richmond discloses an adjustable device designed with one leg insertable into the vagina and another leg bearing against the mons pubis. The Richmond device is specifically designed such that the leg inserted within the vagina is extremely thin, allowing retraction of the vagina for surgical purposes. This is completely opposite to the teachings of the present invention, wherein the leg which is inserted into the vagina is sized and configured to snugly fit within the vagina and includes an inflatable balloon. As such, the present invention is believed distinct from the teachings of Richmond.

U.S. Pat. No. 4,290,420 to Manetta discloses a stress incontinence diagnostic and treatment device including a V-shaped configuration having one leg insertable into the bottom portion of the vagina and the other leg extending forward over the mons pubis and held there by a belt 20. This is different from the teachings of the present invention, wherein one leg is inserted into the vagina and is sized and configured to be snugly received therein and includes an inflatable balloon. Additionally, the present invention is specifically designed to not require any belt to hold it in place.

SUMMARY OF THE INVENTION

The present invention relates to an improved intravaginal incontinence prosthesis. The present invention includes the following interrelated aspects and features:

(A) The inventive intravaginal incontinence prosthesis is disclosed in terms of two embodiments. Each of these embodiments include a structure having a body of generally U-shaped cross-section having two legs connected by a bottom portion.

(B) A first of the legs is sized and configured to be inserted within the vagina of the user a sufficient distance to allow retention therein. With the first leg so inserted in the vagina, a concave chamber thereof faces the direction of the urethra of the user. At least partially contained within this concave chamber is an inflatable balloon-like structure having connected thereto an elongated tube extending through an opening formed through the concave chamber and thence out the vagina for access by the user.

(C) The second leg is sized and configured to engage the mons pubis area and is sufficiently long enough to engage a sufficiently large enough area of the mons pubis area to facilitate retention of the prosthesis in installed position.

(D) The bottom portion connecting the two legs together is designed to overlie the symphysis pubis bone and has a length specifically designed such that with the prosthesis installed with the first leg inserted within the vagina, the length of the bottom portion causes the first leg to be closely adjacent that portion of the vagina adjacent the urethra. Thus, when the balloon-like device is inflated using the tube fluidly connected thereto, engagement of the second leg on the mons pubis prevents backward movement of the first leg thereof, thus allowing more effective compression of the larger portion of the urethra, thereby effectively preventing leakage of urine.

(E) As noted above, the present invention is disclosed herein in terms of two embodiments thereof. In a first embodiment thereof, the legs and bottom portion of the prosthesis are made of an integral construction specifically designed, shaped and configured to conform to the anatomical dimensions of a particular patient. In this embodiment, appropriate measurements of the various anatomical parameters of the patient are made and the one-piece prosthesis is made accordingly. In the second embodiment, the first leg and bottom portion are formed integrally with the second leg being pivotably mounted to the bottom portion thereof with the angle of pivot of the second leg with respect to the bottom portion being adjustable through use of a threaded adjustment member. In this way, the configuration of the second embodiment may be adjusted for patients having different anatomical parameters.

As such, it is a first object of the present invention to provide an improved intravaginal incontinence prosthesis.

It is a further object of the present invention to provide such a prosthesis which is made of a single integral piece.

It is a yet further object of the present invention to provide such an improved intravaginal incontinence prosthesis in a further embodiment wherein one leg is pivotably mounted to the bottom portion and first leg.

It is a still further object of the present invention to provide such a prosthesis including an inflatable balloon allowing pressure to be put on the urethra.

These and other objects, aspects and features of the present invention will be better understood from the following detailed description of the preferred embodiments when read in conjunction with the appended drawing figures.

BRIEF DESCRIPTION OF THE DRAWINGS

FIG. 1 shows a perspective view of a first embodiment of the present invention viewed in a direction toward a front face of a first leg thereof.

FIG. 2 shows a further perspective view of the embodiment of FIG. 1 looking toward a rear face of a second leg thereof.

FIG. 3 shows a cross-sectional view of the embodiment illustrated in FIGS. 1 and 2 illustrated as installed by the patient.

FIG. 4 shows a perspective view of a second embodiment of the present invention looking toward a forward face of a first leg thereof.

FIG. 5 shows a further perspective view of the embodiment illustrated in FIG. 4 looking toward a rear face of a second leg thereof.

FIG. 6 shows a cross-sectional view of the embodiment illustrated in FIGS. 4 and 5 as in use by a patient.

SPECIFIC DESCRIPTION OF THE PREFERRED EMBODIMENTS

With reference, first, to FIGS. 1-3, a first embodiment of the present invention is generally designated by the reference numeral 20. Looking first at FIG. 3, several aspects of the anatomy of the patient will be identified. Shown in FIG. 3 are the vagina 1, the bulbous cavernous muscle 2, the transverse perineal muscle 3, the anus 4, the rectum 5, the end of the spinal column 6, the symphysis pubis 7, the bladder 8, and the urethra 9 and comprises a common wall therebetween.

Also shown in FIG. 3 are the mons pubis 10 and the uterus 11. The vagina 1 is seen to have a rear wall 12 and a forward wall 13 which is adjacent the urethra 9.

Now, turning to FIGS. 1-3, the inventive prosthesis 20 is seen to include a U-shaped body generally designated by the reference numeral 21 having a first leg 23 with a rear face 25 intended to extend toward the rear wall 12 of the vagina and with a forward wall 27 intended to extend toward the forward wall 13 of the vagina and having a concave chamber 29 extending rearwardly therein.

As seen in the figures, the chamber 29 is sized and configured to partially receive an inflatable balloon 31 having an inflation port 33 to which is connected an elongated tube 35 designed to extend out of the vagina 1 and to a position where it may be accessible to the user. The tube 35 has an end 37 distal from the port 33, which end 37 may have a valve, a pump of the bulb type or otherwise, or other air or fluid handling inflation means as appropriate. In any case, the tube 35 is provided to allow filling of the interior of the balloon 31 for a purpose to be described in greater detail hereinafter.

With further reference to FIGS. 1-3, the inventive prosthesis 20 includes a second leg 41 having a rear face 43 adapted to engage the mons pubis 10, a forward face 45 adapted to face away from the user, and a bottom portion 47 which, along with the bottom portion 39 of the first leg 23, interconnect with a bottom portion 51 of the prosthesis 20.

The bottom portion 51 has a length, as best seen in FIG. 3, which is specifically designed to cause the forward face 27 of the first leg 23 to lie in close adjacency to the forward wall 13 of the vagina so that when the balloon 31 is inflated, this close adjacency relationship will be maintained by the rear face 43 of the second leg 41 bearing upon the mons pubis 10. In such configuration, with the balloon 31 inflated, the urethra 9 will be squeezed shut to prevent any flow of urine therefrom in the female incontinent patient.

In the preferred embodiment of the prosthesis 20, it is specifically designed in each case taking into account the specific anatomical parameters of the patient. In creating the prosthesis 20, measurements are made of the various anatomical parameters of the patient which will be taken into account in determining the length of the bottom portion 51 as well as the curvatures of the legs 23 and 41. If desired, plaster of paris may be used on a form to create a prototype from which will be made the final prosthesis 20. Other ways of creating a form for creation of the prosthesis may be used including a bendable form or other techniques. In the preferred embodiment of the prosthesis 20, the prosthesis 20 is made of a material such as an acrylic or polycarbonate plastic in a machining operation wherein all of the appropriate contours of the legs and bottom portion thereof are appropriately formed based upon the measured anatomical parameters of the patient.

In the preferred embodiment of the balloon, the balloon is made of a flexible expansible material such as silicone rubber and the tube 35 is coupled thereto in a usual manner known to those skilled in the art.

With reference, now, to FIGS. 4-6, a second embodiment of the present invention will be described in detail. FIG. 6 shows the same patient as shown in FIG. 3 with the same anatomical structures illustrated using like reference numerals.

With reference to FIGS. 4-6, a second embodiment of the inventive prosthesis is generally designated by the reference numeral 60 and includes a body 61.

A first leg 63 includes a rear face 65, a forward face 67, and a chamber 69 which is concave in nature and is designed to receive the balloon 71 having a port 73 to which is coupled an elongated tube 75 having a fitting 77 at an end thereof remote from the port 73, which fitting 77 may be attached to a pump device, a valve, or other air or fluid handling accessory. Alternatively, the balloon 71 may have the port 73 located in a manner corresponding to the manner of location of the port 33 of the balloon 31 illustrated in FIGS. 1-3, with an opening (not shown) being formed through the leg 63 in a manner similar to the opening 34 formed in the leg 23 allowing the tube 75 to extend therethrough.

The second leg 81 includes a rearward facing face 83, a forward facing face 85, and a bottom section 87.

Turning back to the first leg 63, the first leg 63 includes a bottom section 79 which integrally connects with a bottom portion 90. The second leg 81 includes a bottom section 88 pivotably, mounted to the bottom portion 90 at adjustment means including the pivot pin 91.

The bottom portion 90 includes a threaded recess 92 in which may be threadably received the threaded rod portion of a fastener 93 extending through a large non-threaded opening 86 in the bottom section 88 of the second leg 81 and thence into the threaded passage 92 in the bottom portion 90.

The bottom section 88 of the second leg 81 includes a shoulder 84 against which the head 95 of the fastener 93 may bear, thus resulting in rotative movements of the fastener 93 causing pivoting of the second leg 81 to differing orientations with respect to the bottom portion 90 and the first leg 63 responsive to movements of the fastener 93 in or out through rotative movements thereof and engagement of the head 95 thereof against the shoulder 84. As should be understood, best, from FIG. 6, different pivotable orientations of the leg 81 with respect to the leg 63 will result in the distance between the top 82 of the leg 81 and the top 64 of the leg 63 changing, thereby effectively allowing adaptation of the prosthesis 60 for women having differing anatomical characteristics.

The preferred materials for construction of the prosthesis 60 and balloon 71 are the same as those for the prosthesis 20, except that the fastener 93 may be made of a metallic material and the threaded bore 92 of the bottom portion 90 may be created by embedding a threaded metallic sleeve therein.

As such, an invention has been described in terms of a preferred embodiment thereof which fulfills each and every one of the objects of the invention as set forth hereinabove and provides a new and improved intravaginal incontinence prosthesis in two embodiments thereof having great novelty and utility.

Of course, various changes, modifications and alterations in the teachings of the present invention may be contemplated by those skilled in the art without departing from the intended spirit and scope thereof. As such, it is intended that the present invention only be limited by the terms of the appended claims.

I claim:

1. An improved prosthesis for use with a woman having a vagina, urethra, mons pubis and symphysis pubis, said prosthesis comprising:
    (a) a first leg sized and configured to be received in said vagina, said first leg having a chamber;
    (b) a second leg connected to said first leg via a bottom portion and configured to bear against said mons pubis when said first leg is within said vagina;
    (c) an inflatable balloon at least partially contained within said chamber and having a bottom wall remote from said chamber and engaging a common wall separating said vagina and urethra when said first leg is within said vagina; and
    (d) inflation means for selectively inflating said balloon to compress said urethra and thereby prevent undesired urine leakage, engagement of said second leg on said mons pubis maintaining pressure of said balloon on said common wall.

2. The invention of claim 1, wherein said chamber has a first opening allowing protrusion of said balloon therefrom and a second opening, said inflation means including a tube extending through said second opening and in fluid communication with said balloon.

3. The invention of claim 1, wherein said prosthesis is made of plastic and said balloon is made of rubber.

4. The invention of claim 1, wherein said bottom portion is integral with said first leg.

5. The invention of claim 4, wherein said bottom portion is integral with said second leg.

6. The invention of claim 4, wherein said second leg is pivotably attached to said bottom portion.

7. The invention of claim 6, wherein adjustment means is operative to allow adjustment of an angular relationship between said second leg and said bottom portion, whereby said prosthesis may be used by women of differing anatomical characteristics.

* * * * *